(12) United States Patent
Bono et al.

(10) Patent No.: US 9,232,953 B2
(45) Date of Patent: Jan. 12, 2016

(54) CUTTING TOOL FOR BONE, CARTILAGE, AND DISK REMOVAL

(71) Applicant: Peter Bono, Franklin, MI (US)

(72) Inventors: Peter Bono, Franklin, MI (US); James D. Lark, II, West Bloomfield, MI (US); Anthony J. Ruhala, Almont, MI (US)

(73) Assignee: Peter Bono, Franklin, MI (US)

( * ) Notice: Subject to any disclaimer, the term of this patent is extended or adjusted under 35 U.S.C. 154(b) by 422 days.

(21) Appl. No.: 13/647,101

(22) Filed: Oct. 8, 2012

(65) Prior Publication Data
US 2014/0100574 A1 Apr. 10, 2014

(51) Int. Cl.
*A61B 17/16* (2006.01)
*A61B 17/32* (2006.01)

(52) U.S. Cl.
CPC ......... *A61B 17/1615* (2013.01); *A61B 17/1671* (2013.01); *A61B 17/32002* (2013.01); *A61B 2017/1602* (2013.01)

(58) Field of Classification Search
CPC .................... A61B 17/32002; A61B 17/1761; A61B 17/1615
USPC .............. 606/79, 80; 408/223, 224, 227, 229, 408/230
See application file for complete search history.

(56) References Cited

U.S. PATENT DOCUMENTS

| | | | |
|---|---|---|---|
| 2,825,186 A | 3/1958 | Palush | |
| 2,834,158 A | 5/1958 | Petermann | |
| 3,058,199 A * | 10/1962 | Cave et al. | 407/54 |
| 3,554,197 A | 1/1971 | Dobbie | |
| 4,008,720 A | 2/1977 | Brinckmann et al. | |
| 4,197,645 A | 4/1980 | Scheicher | |
| D262,630 S * | 1/1982 | Logan, Jr. | D15/139 |
| 4,556,347 A * | 12/1985 | Barish | 408/230 |
| 4,596,243 A | 6/1986 | Bray | |
| 5,092,875 A | 3/1992 | McLees | |
| 5,478,176 A * | 12/1995 | Stedt et al. | 408/59 |
| 5,626,444 A * | 5/1997 | Campian | 407/54 |
| 5,843,110 A | 12/1998 | Dross et al. | |
| 6,110,174 A | 8/2000 | Nichter | |

(Continued)

FOREIGN PATENT DOCUMENTS

WO 2009151926 A2 12/2009

OTHER PUBLICATIONS

International Search Report and Written Opinion for corresponding Application No. PCT/US2013/063182, mailed Jan. 10, 2014, 15 pages.

(Continued)

*Primary Examiner* — Anu Ramana
(74) *Attorney, Agent, or Firm* — McHale & Slavin, P.A.

(57) ABSTRACT

A cutting tool for bone, cartilage, and disk removal includes a body with a first radial array of helical flutes formed along the body with a continuous radius in a first helical direction. The body has a second radial array of helical flutes formed along the body with a continuous radius in a second helical direction opposed to the first helical direction and intersecting the first array of helical flutes. Each helical flute forms a pair of spaced apart rake surfaces, which collectively perform a first and second cutting operations along a side of the body such that the intersecting rakes balance the cutting operation thereby minimizing axial loading of the cutting tool to permit bidirectional cutting while minimizing g inadvertent axial translation of the tool.

19 Claims, 4 Drawing Sheets

(56) References Cited

U.S. PATENT DOCUMENTS

| | | | |
|---|---|---|---|
| 6,234,725 B1 * | 5/2001 | Campian | 407/54 |
| 6,267,542 B1 * | 7/2001 | Salmon | 408/223 |
| 6,498,421 B1 | 12/2002 | Oh et al. | |
| 6,966,912 B2 | 11/2005 | Michelson | |
| 7,090,442 B2 * | 8/2006 | Ahrnkiel et al. | 407/29.12 |
| 7,160,304 B2 | 1/2007 | Michelson | |
| 7,387,612 B2 | 6/2008 | Pal et al. | |
| 7,717,710 B2 | 5/2010 | Danger et al. | |
| 7,922,720 B2 | 4/2011 | May et al. | |
| 8,025,662 B2 * | 9/2011 | Knisely et al. | 606/80 |
| 8,353,912 B2 | 1/2013 | Darian et al. | |
| 8,480,673 B2 | 7/2013 | Yedlicka et al. | |
| 2004/0147934 A1 | 7/2004 | Kiester | |
| 2005/0273127 A1 | 12/2005 | Novak et al. | |
| 2005/0283175 A1 | 12/2005 | Tanner et al. | |
| 2006/0235305 A1 | 10/2006 | Cotter et al. | |
| 2006/0235306 A1 | 10/2006 | Cotter et al. | |
| 2007/0093841 A1 | 4/2007 | Hoogland | |
| 2007/0282344 A1 | 12/2007 | Yedlicka et al. | |
| 2007/0282345 A1 | 12/2007 | Yedlicka et al. | |
| 2009/0024129 A1 | 1/2009 | Gordon et al. | |
| 2010/0145343 A1 | 6/2010 | Johnson et al. | |
| 2010/0256644 A1 | 10/2010 | Stearns et al. | |
| 2011/0015635 A1 | 1/2011 | Aryan | |
| 2011/0196404 A1 | 8/2011 | Dietz et al. | |
| 2011/0295270 A1 | 12/2011 | Giordano et al. | |
| 2012/0265206 A1 | 10/2012 | Jang et al. | |
| 2014/0277028 A1 | 9/2014 | Voic | |
| 2015/0057664 A1 | 2/2015 | Scianamblo | |

OTHER PUBLICATIONS

Master Cut Tool Corp., Dental Lab, 2010 Bur Series—Metric, 4 pages.

"News & Notes", British Dental Journal, vol. 191, No. 7, Oct. 13, 2001, pp. 410-411.

http://www.Izqtool.com/include/search.aspx?keycode=c-grade&type=1&language=en, Feb. 4, 2011, 7 pages.

http://www.chinatungsten.com, "Pictures of Tungsten Carbide Drills, Mills and Burrs", Feb. 11, 2010, 1 page.

* cited by examiner

CUTTING TOOL FOR BONE, CARTILAGE, AND DISK REMOVAL

TECHNICAL FIELD

Various embodiments relate to rotary oscillating bone, cartilage, and disk removal cutting tools.

BACKGROUND

The prior art has provided rotary bone, cartilage, and disk removal cutting tools. The prior art has also provided rotary oscillating bone, cartilage, and disk removal tool assemblies.

SUMMARY

According to at least one embodiment, a cutting tool for bone, cartilage, and disk removal includes a shank sized to be received in a rotary power tool for oscillatory rotation about the shank at a limited angular range of rotation to minimize any form of change to soft materials during material removal of bone, cartilage, and disk. A body is provided on a distal end of the shank. The body has a first radial array of helical flutes formed along the body with a continuous radius in a first helical direction. Each helical flute of the first array forms a pair of spaced apart rake surfaces along the flute. The body has a second radial array of helical flutes formed along the body with a continuous radius in a second helical direction opposed to the first helical direction and intersecting the first array of helical flutes. Each helical flute of the second array forms a pair of spaced apart rake surfaces along the flute. The rake surfaces of the first and second arrays of helical flutes collectively perform a first cutting operation along a side of the body in a first rotational direction of the shank such that the intersecting rakes balance the cutting operation thereby minimizing axial loading of the cutting tool. The rake surfaces of the first and second arrays of helical flutes collectively perform a second cutting operation along the side of the body in a second rotational direction of the shank such that the intersecting rakes balance the cutting operations thereby minimizing axial loading of the cutting tool to permit bidirectional cutting while minimizing inadvertent axial translation of the tool.

According to at least another embodiment, a power tool assembly for bone, cartilage, and disk removal includes a rotary power tool for oscillatory rotation at a limited angular range of rotation. A cutting tool for bone, cartilage, and disk removal includes a shank received in the rotary power tool for oscillatory rotation about the shank at the limited angular range of rotation to minimize any form of change to soft materials during material removal of bone, cartilage, and disk. A body is provided on a distal end of the shank. The body has a first radial array of helical flutes formed along the body with a continuous radius in a first helical direction. Each helical flute of the first array forms a pair of spaced apart rake surfaces along the flute. The body has a second radial array of helical flutes formed along the body with a continuous radius in a second helical direction opposed to the first helical direction and intersecting the first array of helical flutes. Each helical flute of the second array forms a pair of spaced apart rake surfaces along the flute. The rake surfaces of the first and second arrays of helical flutes collectively perform a first cutting operation along a side of the body in a first rotational direction of the shank such that the intersecting rakes balance the cutting operation thereby minimizing axial loading of the cutting tool. The rake surfaces of the first and second arrays of helical flutes collectively perform a second cutting operation along the side of the body in a second rotational direction of the shank such that the intersecting rakes balance the cutting operations thereby minimizing axial loading of the cutting tool to permit bidirectional cutting while minimizing inadvertent axial translation of the tool.

According to another embodiment, a method to remove at least one of bone, cartilage, and disk obtains a power tool assembly for bone, cartilage, and disk removal. The power tool assembly includes a rotary power tool for oscillatory rotation at a limited angular range of rotation. A cutting tool for bone, cartilage, and disk removal includes a shank received in the rotary power tool for oscillatory rotation about the shank at the limited angular range of rotation to minimize any form of change to soft materials during material removal of bone, cartilage, and disk. A body is provided on a distal end of the shank. The body has a first radial array of helical flutes formed along the body with a continuous radius in a first helical direction. Each helical flute of the first array forms a pair of spaced apart rake surfaces along the flute. The body has a second radial array of helical flutes formed along the body with a continuous radius in a second helical direction opposed to the first helical direction and intersecting the first array of helical flutes. Each helical flute of the second array forms a pair of spaced apart rake surfaces along the flute. The rake surfaces of the first and second arrays of helical flutes collectively perform a first cutting operation along a side of the body in a first rotational direction of the shank such that the intersecting rakes balance the cutting operation thereby minimizing axial loading of the cutting tool. The rake surfaces of the first and second arrays of helical flutes collectively perform a second cutting operation along the side of the body in a second rotational direction of the shank such that the intersecting rakes balance the cutting operations thereby minimizing axial loading of the cutting tool to permit bidirectional cutting while minimizing inadvertent axial translation of the tool. The power tool is operated to oscillate the cutting tool. The oscillating cutting tool is applied to at least one of bone, cartilage, and disk for material removal.

According to at least another embodiment, a cutting tool for bone, cartilage, and disk removal includes a shank sized to be received in a rotary power tool for oscillatory rotation about the shank at a limited angular range of rotation to minimize any form of change to soft materials during material removal of bone, cartilage, and disk. A body is provided on a distal end of the shank. The body has first and second opposed direction and equivalent radial arrays of helical flutes formed therein forming a pair of spaced apart rake surfaces along each flute, to perform bidirectional cutting operations along a side of the body such that the intersecting rakes balance the cutting operations thereby minimizing axial loading of the cutting tool, to permit bidirectional cutting while minimizing inadvertent axial translation of the tool.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
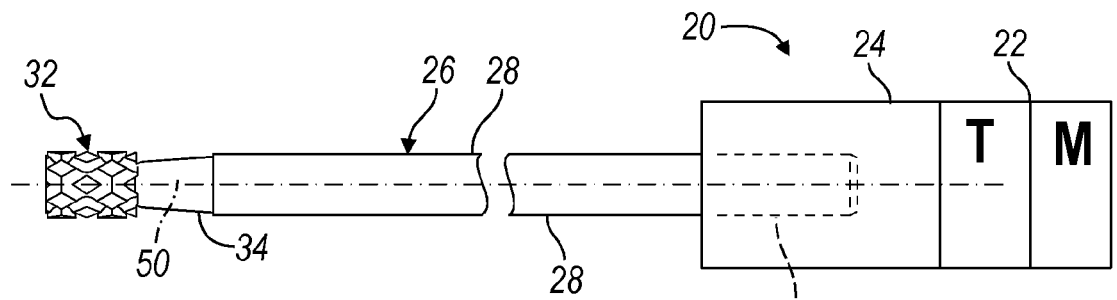
FIG. 1 is a schematic view of a power tool assembly according to an embodiment, illustrated with a cutting tool according to another embodiment.
Figure 2:
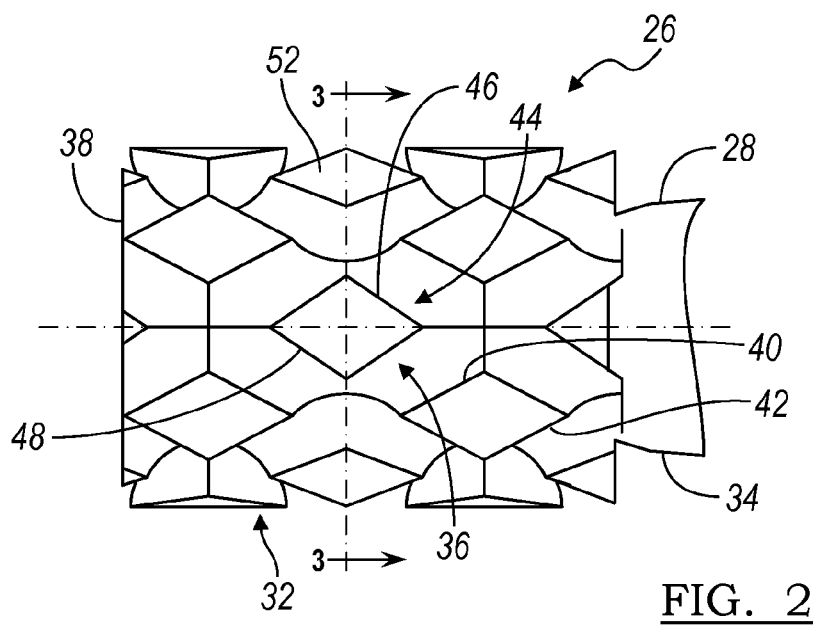
FIG. 2 is an enlarged side view of a body of the cutting tool of FIG. 1.

With reference now to FIG. 1, a rotary oscillating bone, cartilage, and disk removal tool assembly is illustrated according to an embodiment, and referenced generally by numeral 20. The bone, cartilage, and disk removal tool assembly 20 is a handheld tool assembly with a housing 22 providing a handle for manual gripping for bone, cartilage, and disk removal via a cutting operation. The tool assembly 20 can be used in surgical operations, such as spinal surgery, wherein bone, cartilage, disk, and other non-fibrous body material may be removed, such as from the spine. The tool assembly includes a motor M in the housing 22 for driving a transmission T. The transmission T is connected to a tool holder 24, which receives and supports a cutting tool 26. The tool holder 24 may be a collet, a chuck or the like.

The tool assembly 20 rotates the tool holder 24, and consequently the cutting tool 26, in both directions such that the cutting tool 26 rotary oscillates about its axis. The cutting tool 26 is driven to rotate partially in both directions with a limited angular range of rotation. Such oscillatory cutting is effective for bone, cartilage, and disk removal by a shearing operation, while effective in minimizing damage, abrasion, cutting, material removal, or any form of change to any soft or fibrous material. If the cutting tool 26 inadvertently contacts fibrous material, such as a nerve, during the cutting operation, the fibrous material is likely to be oscillated due to the flexibility of the fibrous material with minimal shearing, thereby minimizing damage to the fibrous material. Such rotary oscillating operations are common in cast removal tools.

The cutting tool 26 includes a shank 28 that is sized to be supported within the tool holder 24 at a proximal end 30 of the tool 26. According to one example, the shank 28 may have a diameter of 3.175 millimeters (mm) and a length of approximately 127.6 mm. The cutting tool 26 includes a body 32 at a distal end 34 of the shank 28. The distal end of the shank 28 may taper to a diameter of approximately 2.2 mm in the last 5.9 mm of the distal end 34.

The body 32 is illustrated in greater detail in FIGS. 2-5. The body 32 may have an axial length of approximately 4.4 mm with a diameter of approximately 3.175 mm according to at least one embodiment. The body 32 has a first radial array of helical flutes 36 formed along the body 32 with a continuous radius in a first helical direction, which is counter-clockwise from a distal end 38 of the body to the shank distal end 34 when viewed axially from the body distal end 38. Each helical flute 36 of the first array forms a pair of spaced apart rake surfaces 40, 42 along the flute 36.

A second radial array of helical flutes 44 is formed along the body 32 with a continuous radius in a second helical direction that is opposed to the first helical direction. In other words, the second helical direction is clockwise from the body distal end 38 to the shank distal end 34 when viewed axially from the body distal end 38. The second array of helical flutes 44 intersects the first array of helical flutes 36. Each helical flute 44 of the second array also forms a pair of spaced apart rake surfaces 46, 48 along the flute 44.

The rake surfaces 40, 42, 46, 48 of the first and second radial arrays of helical flutes 36, 44 collectively perform a first cutting operation along a side of the body 32 in a first rotational direction of the shank 28 (counter-clockwise in FIG. 3) such that the intersecting rakes 40, 46 balance the cutting operation thereby minimizing axial loading of the cutting tool 26. The rake surfaces 40, 42, 46, 48 of the first and second radial arrays of helical flutes 36, 44 also collectively perform a second cutting operation along a side of the body 32 in a second rotational direction of the shank 28 (clockwise in FIG. 3) such that the intersecting rakes 42, 48 balance the cutting operation thereby minimizing axial loading of the cutting tool 26. Moreover, the rake surfaces 40, 42, 46, 48 of the first and second radial arrays of helical flutes 36, 44 permit bidirectional cutting while minimizing inadvertent axial translation of the tool 26. Additionally, the balanced cutting also minimizes rotary loading, thereby minimizing "walking" or inadvertent lateral translation of the tool 26.

Figure 3:
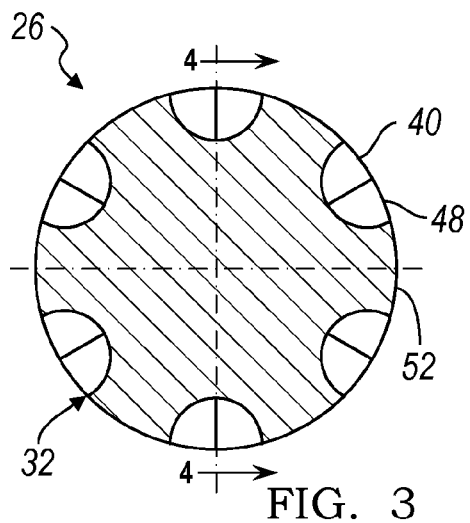
FIG. 3 is a section view taken along line 3-3 of FIG. 2.
Figure 4:
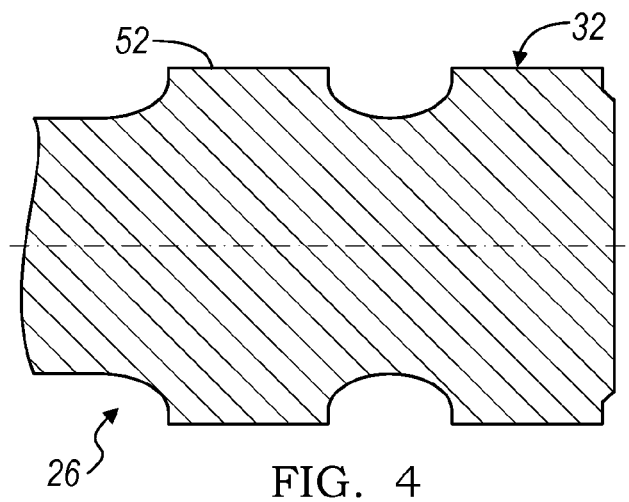
FIG. 4 is a section view taken along line 4-4 of FIG. 3.
Figure 5:
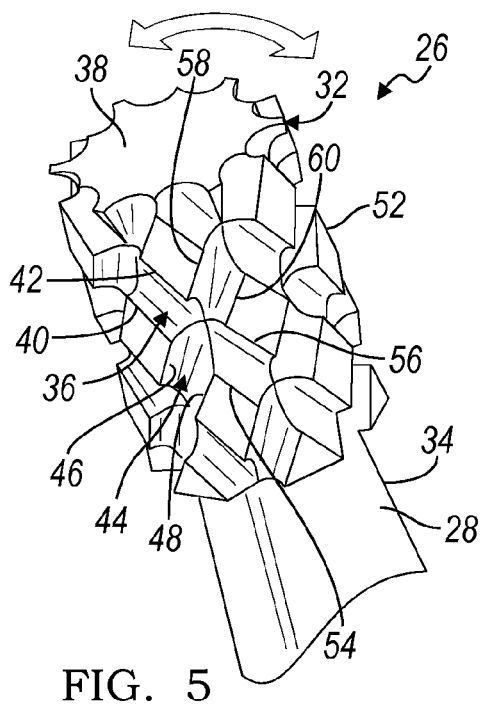
FIG. 5 is a perspective view of the cutting tool body of FIG. 2.

The first array of helical flutes 36 and the second array of helical flutes 44 may have a common cross section as illustrated in FIG. 3, which may be round or formed with a radius of 0.4 mm according to an embodiment. Each flute 36 of the first array are oriented at a first helical angle relative to a rotational axis 50 (FIG. 1) of the cutting tool 26. The second array of helical flutes 44 may also be oriented a second angle relative to the rotational axis 50 of the cutting tool 26, which may be a negative value of the first angle.

The first array of helical flutes 36 is spaced circumferentially to provide a radial array of lands 52 between the first array of helical flutes 36. Likewise, the second array of helical flutes 44 is spaced circumferentially defining the lands 52. The spacing of the arrays of flutes 36, 44 may be generally equivalent according to an embodiment. A plurality of relief surfaces 54, 56, 58, 60 may each be provided on the lands 52 adjacent to the rake surfaces 40, 42, 46, 48 respectively. The relief surfaces 54, 56, 58, 60 may each be generally equivalent in size. The relief surfaces 54, 56, 58, 60 may each be curved, by a radius of approximately two mm, for example. The relief surfaces 54, 56, 58, 60 may be collectively formed as one curved surface upon each entire land 52 such that there is not a cylindrical bearing surface upon the lands 52.

All features of the body 32 may be symmetrical for balancing the cutting operations to minimize axial inadvertent axial translation and lateral translation of the cutting tool 26. Suitable cutting operations may be obtained by asymmetrical geometries as well.

The cutting tool of FIGS. 1-5 is illustrated with a body 32 configured for side cutting only. FIGS. 6-14 illustrate various embodiments, wherein like elements retain like reference numerals; and new elements are assigned new reference numerals.

Figure 6:
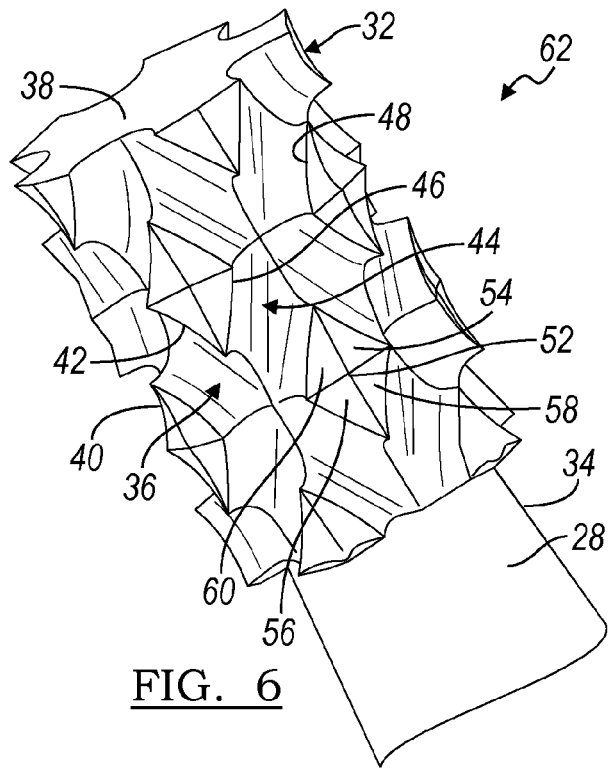
FIG. 6 is a perspective view of a cutting tool body according to another embodiment.

FIG. 6 illustrates another cutting tool 62 with separate relief surfaces 54, 56, 58, 60 providing four facets upon each land 52.

Figure 7:
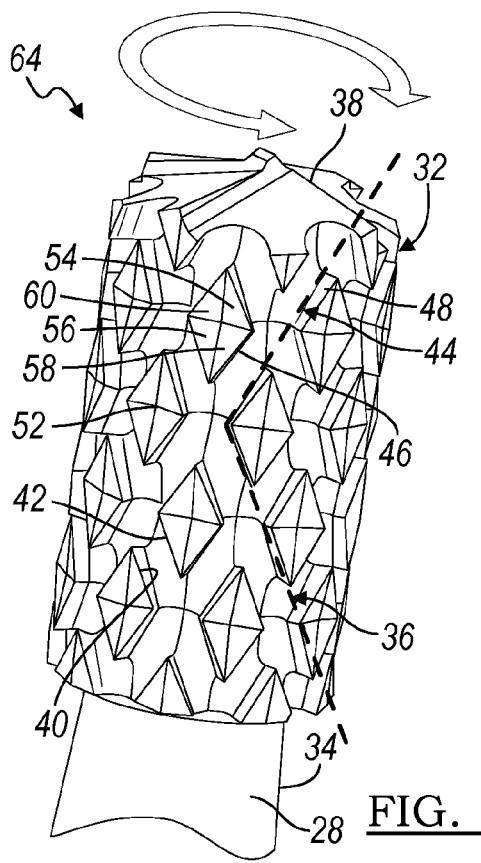
FIG. 7 is a perspective view of a cutting tool body according to another embodiment.

FIG. 7 illustrates another cutting tool 64 with narrower flutes 36, 44 resulting in more rake surfaces 40, 42, 46, 48. Additionally, a conical array of rake surfaces 66 is provided on the body distal end 38 for providing an end cutting operation in both rotary directions.

Figure 8:
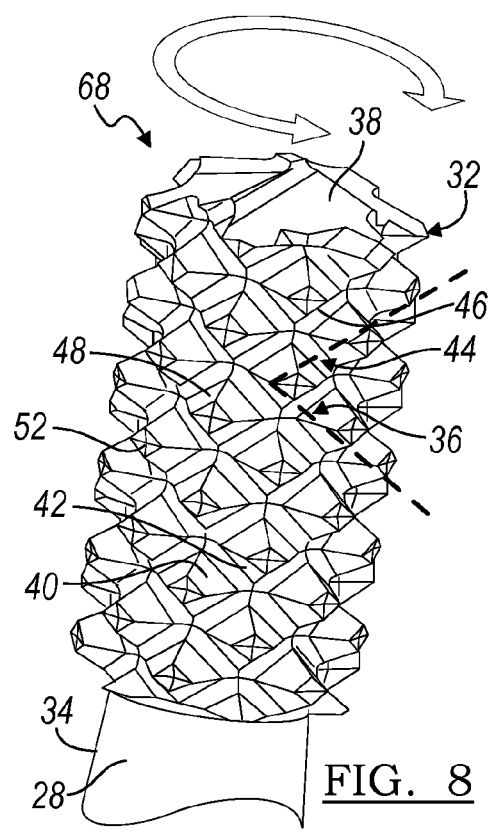
FIG. 8 is a perspective view of a cutting tool body according to yet another embodiment.

FIG. 8 illustrates another cutting tool 68 with a larger angle for the arrays of helical flutes 36, 44.

Figure 9:
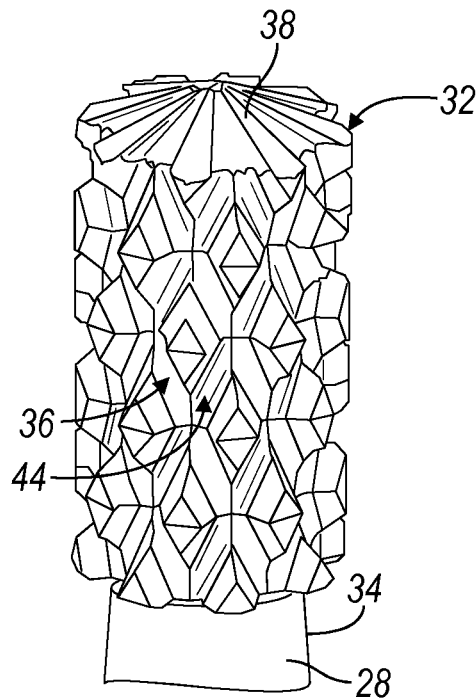
FIG. 9 is a perspective view of a cutting tool body according to another embodiment.
Figure 10:
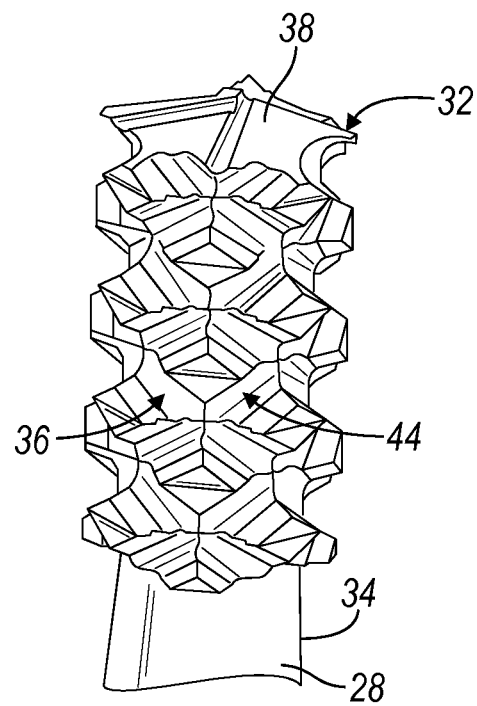
FIG. 10 is a perspective view of a cutting tool body according to another embodiment.
Figure 11:
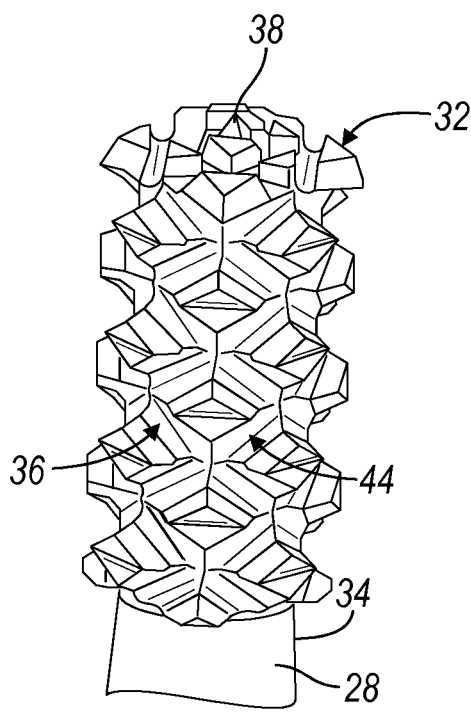
FIG. 11 is a perspective view of a cutting tool body according to yet another embodiment.
Figure 12:
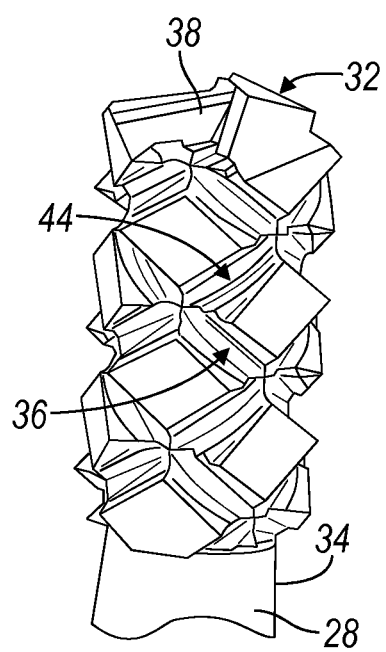
FIG. 12 is a perspective view of a cutting tool body according to another embodiment.
Figure 13:
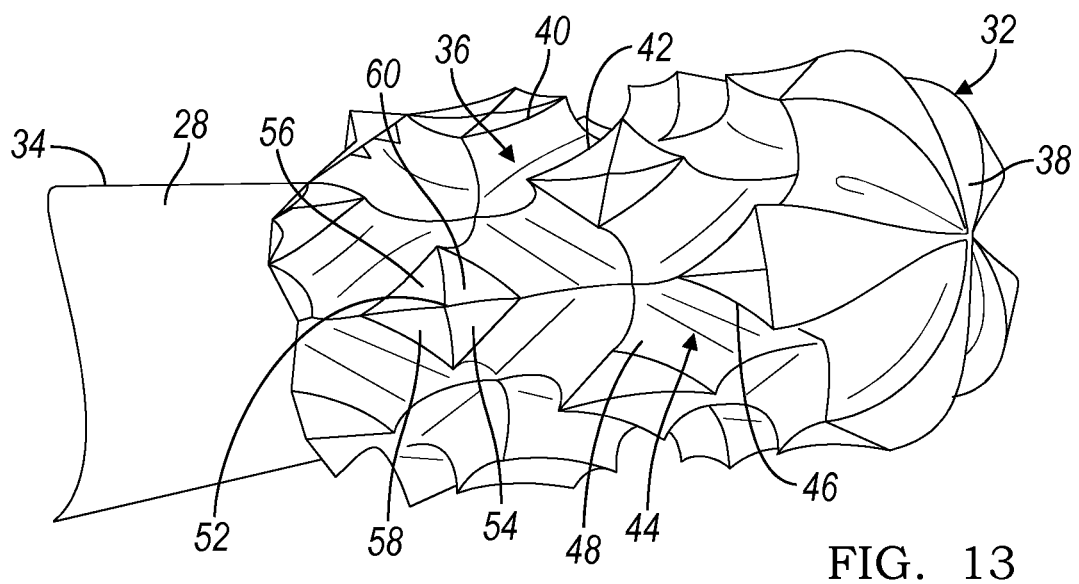
FIG. 13 is a perspective view of a cutting tool body according to another embodiment.
Figure 14:
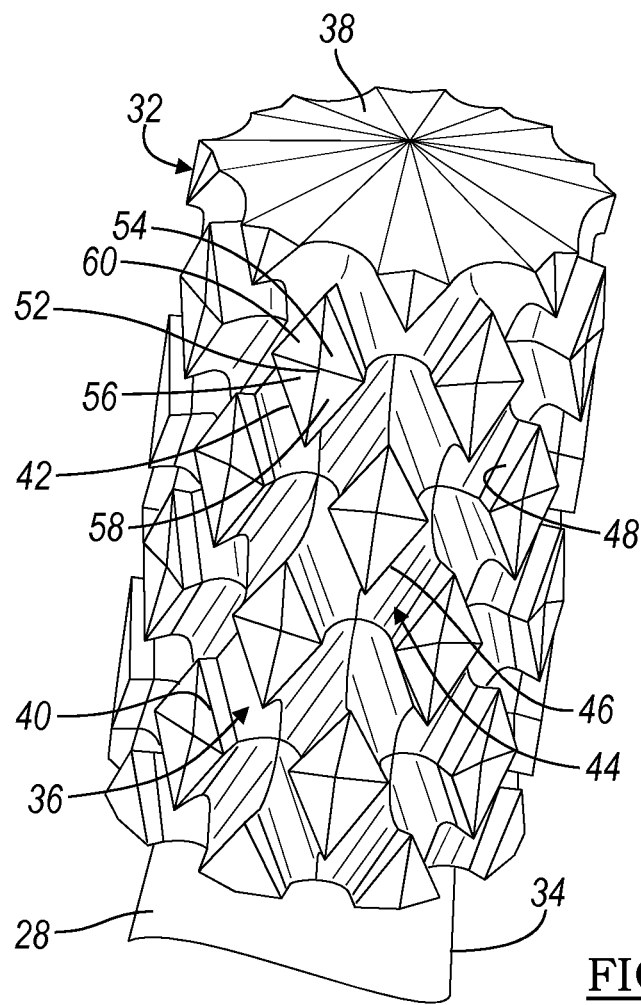
FIG. 14 is a perspective view of a cutting tool body according to yet another embodiment.

FIG. 9 illustrates another cutting tool 70 with rake surfaces 66 on the body distal end 38 that are aligned angularly with the flutes 36, 44.

FIGS. 10-14 illustrate cutting tools 72, 74, 76, 78, 80 depicting various examples of combinations of geometries for the body 32 and corresponding rake and relief surfaces 40, 42, 46, 48, 54, 56, 58, 60, 66. Of course various other geometries and combinations can be obtained as other embodiments.

While various embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A cutting tool for bone, cartilage, and disk removal comprising:
    a shank sized to be received in a rotary power tool for oscillatory rotation about the shank at a limited angular range of rotation to minimize any form of change to soft materials during material removal of bone, cartilage, and disk; and
    a body provided on a distal end of the shank, the body having a first radial array of helical flutes formed along the body with concave surfaces in a first helical direction, each helical flute of the first array forming a pair of spaced apart rake surfaces along the flute, said first array of rake surfaces being constructed and arranged to cut said soft materials when said shank is rotated in a first direction, the body having a second radial array of helical flutes formed along the body with concave surfaces in a second helical direction opposed to the first helical direction and intersecting the first array of helical flutes, each helical flute of the second array forming a pair of spaced apart rake surfaces along the flute, said second array of rake surfaces being constructed and arranged to cut said soft materials when said shank is rotated in a second direction, the second direction opposite to the first direction, to provide bidirectional cutting while minimizing inadvertent axial translation of the tool.

2. The cutting tool of claim 1 wherein the first array of helical flutes each have substantially the same cross section as that of the second array of helical flutes.

3. The cutting tool of claim 1 wherein the first array of helical flutes are each oriented at a first angle relative to a rotational axis of the cutting tool; and
    wherein the second array of helical flutes are each oriented a second angle relative to the rotational axis of the cutting tool, the second angle being a negative value of the first angle.

4. The cutting tool of claim 1 wherein the first array of helical flutes each have a round cross section.

5. The cutting tool of claim 4 wherein the second array of helical flutes each have a round cross section having a radius that is generally equivalent to a radius of the first array of helical flutes.

6. The cutting tool of claim 1 wherein the first array of helical flutes are spaced circumferentially to provide a radial array of lands between the first array of helical flutes.

7. The cutting tool of claim 6 wherein the second array of helical flutes are spaced circumferentially; and
    wherein the spacing of the first array of helical flutes is generally equivalent to the spacing of the second array of helical flutes.

8. The cutting tool of claim 6 wherein the second array of helical flutes are spaced circumferentially;
    wherein a first plurality of relief surfaces are provided on the radial array of lands adjacent to the rake surfaces of the first array of helical flutes; and
    wherein a second plurality of relief surfaces are provided on the radial array of lands adjacent to the rake surfaces of the second array of helical flutes.

9. The cutting tool of claim 8 wherein the second plurality of relief surfaces are generally equivalent in size with the first plurality of relief surfaces.

10. The cutting tool of claim 8 wherein the first plurality of relief surfaces and the second plurality of relief surfaces are each curved.

11. The cutting tool of claim 8 wherein the first plurality of relief surfaces and the second plurality of relief surfaces each having a radius of approximately two millimeters.

12. The cutting tool of claim 6 wherein a plurality of relief surfaces are provided on the radial array of lands adjacent to the rake surfaces of the first array of helical flutes.

13. The cutting tool of claim 12 wherein the plurality of relief surfaces are each curved.

14. The cutting tool of claim 13 wherein the plurality of relief surfaces each have a radius of approximately two millimeters.

15. The cutting tool of claim 1 wherein the body does not comprise a cylindrical bearing surface.

16. The cutting tool of claim 1 wherein the intersecting rakes balance the cutting operations thereby minimizing rotary loading of the cutting tool to permit bidirectional cutting while minimizing inadvertent lateral translation of the tool.

17. The cutting tool of claim 1 wherein at least one rake is formed into a distal end of the body to perform an end cutting operation.

18. A power tool assembly for bone, cartilage, and disk removal comprising:
    a rotary power tool for oscillatory rotation at a limited angular range of rotation; and
    a cutting tool according to claim 1.

19. A cutting tool for bone, cartilage, and disk removal comprising:
    a shank sized to be received in a rotary power tool for oscillatory rotation about the shank at a limited angular range of rotation to minimize any form of change to soft materials during material removal of bone, cartilage, and disk; and
    a body provided on a distal end of the shank, the body having first and second opposed radial arrays of helical flutes formed therein forming a pair of spaced apart rake surfaces along opposed sides of each flute, said first rake surfaces being constructed and arranged to cut said soft materials when said shank is rotated in a first direction while said second rake surfaces are constructed and arranged to cut said soft materials when said shank is rotated in a second direction, the second direction opposite to the first direction, to perform bidirectional cutting operations along a side of the body such that the intersecting rakes balance the cutting operations thereby minimizing axial loading of the cutting tool, to permit bidirectional cutting while minimizing inadvertent axial translation of the tool.

* * * * *